(12) United States Patent
Koyata et al.

(10) Patent No.: US 10,677,695 B2
(45) Date of Patent: Jun. 9, 2020

(54) MAGNETIC MATERIAL FOR COLLECTING MAGNETIC PARTICLES AND UTILIZATION THEREOF

(71) Applicant: LSI Medience Corporation, Tokyo (JP)

(72) Inventors: Atsushi Koyata, Tokyo (JP); Takaaki Sorin, Kamakura (JP)

(73) Assignee: LSI Medience Corporation, Tokyo (JP)

( * ) Notice: Subject to any disclaimer, the term of this patent is extended or adjusted under 35 U.S.C. 154(b) by 820 days.

(21) Appl. No.: 14/478,345

(22) Filed: Sep. 5, 2014

(65) Prior Publication Data

US 2014/0377882 A1     Dec. 25, 2014

Related U.S. Application Data

(60) Division of application No. 11/121,937, filed on May 5, 2005, now abandoned, which is a continuation of (Continued)

(30) Foreign Application Priority Data

Nov. 7, 2002  (JP) .................................. 2002-324177

(51) Int. Cl.
*G01N 1/40* (2006.01)
*B03C 1/28* (2006.01)
(Continued)

(52) U.S. Cl.
CPC .............. *G01N 1/405* (2013.01); *B03C 1/288* (2013.01); *G01N 33/553* (2013.01); *G01N 35/0098* (2013.01)

(58) Field of Classification Search
CPC .. G01N 1/405; G01N 33/553; G01N 35/0098; B03C 1/288
See application file for complete search history.

(56) References Cited

U.S. PATENT DOCUMENTS

| | | |
|---|---|---|
| 4,988,618 A | 1/1991 | Li et al. |
| 5,424,703 A | 6/1995 | Blume, Jr. |

(Continued)

FOREIGN PATENT DOCUMENTS

| | | |
|---|---|---|
| JP | 2-54594 U1 | 4/1990 |
| JP | 8-62224 A | 3/1996 |

(Continued)

OTHER PUBLICATIONS

Guowei Feng, et al., "Magia 120L Chemiluminescent enzyme immunoassay equipment and clinical application thereof", Modern Medical Equipment and Application 2000, 12(4): 8-10.

(Continued)

*Primary Examiner* — Melanie Brown
(74) *Attorney, Agent, or Firm* — Oblon, McClelland, Maier & Neustadt, L.L.P.

(57) ABSTRACT

For collecting magnetic particles, there is used a magnetic material including a plurality of magnets that are arranged in contact one with another in parallel to a direction of magnetization in such a manner that south and north poles of adjacent magnets are reversed alternately or a magnetic material having at least one peak of a magnetic force in a magnetic pole surface, and the peak magnetic force is 600 gausses or more.

6 Claims, 5 Drawing Sheets

Related U.S. Application Data application No. PCT/JP03/14203, filed on Nov. 7, 2003.

(51) Int. Cl.
*G01N 33/553* (2006.01)
*G01N 35/00* (2006.01)

(56) References Cited

U.S. PATENT DOCUMENTS

| | | | |
|---|---|---|---|
| 5,647,994 A * | 7/1997 | Tuunanen | B03C 1/288 |
| | | | 210/222 |
| 5,702,950 A | 12/1997 | Tajima | |
| 5,837,144 A | 11/1998 | Bienhaus et al. | |
| 5,898,352 A | 4/1999 | McEachern et al. | |
| 6,036,857 A * | 3/2000 | Chen | B03C 1/035 |
| | | | 210/222 |
| 6,096,554 A | 8/2000 | Tajima | |
| 6,100,079 A | 8/2000 | Tajima | |
| 6,132,607 A | 10/2000 | Chen et al. | |
| 6,133,037 A | 10/2000 | Tajima | |
| 6,231,814 B1 | 5/2001 | Tajima | |
| 6,292,680 B1 | 9/2001 | Somogyi et al. | |
| 6,331,277 B2 | 12/2001 | Tajima | |
| 6,447,729 B1 | 9/2002 | Tuunanen | |
| 6,509,193 B1 | 1/2003 | Tajima | |
| 2002/0084225 A1 * | 7/2002 | Hatch | B01L 3/5085 |
| | | | 210/695 |
| 2003/0138819 A1 * | 7/2003 | Gong | B01L 3/5027 |
| | | | 435/6.11 |

FOREIGN PATENT DOCUMENTS

| | | |
|---|---|---|
| JP | 08-304399 | 11/1996 |
| JP | 09-297140 | 11/1997 |
| JP | 10-68731 | 3/1998 |
| JP | 11-125601 | 5/1999 |
| JP | 3013937 | 12/1999 |
| JP | 3115501 | 9/2000 |
| JP | 3128541 | 11/2000 |
| JP | 2002-503548 | 2/2002 |
| JP | 3658857 | 3/2005 |
| WO | WO 92/14138 | 8/1992 |
| WO | WO 92/14139 | 8/1992 |
| WO | WO 97/31105 A1 | 8/1997 |
| WO | WO 97/44671 | 11/1997 |
| WO | WO 99/42219 | 8/1999 |

OTHER PUBLICATIONS

Office Action dated Jun. 19, 2012 in Japanese Patent Application No. 2010-118846 (with English language translation).

* cited by examiner

MAGNETIC MATERIAL FOR COLLECTING MAGNETIC PARTICLES AND UTILIZATION THEREOF

CROSS-REFERENCE TO RELATED APPLICATIONS

The present application is a divisional of U.S. application Ser. No. 11/121,937, filed on May 5, 2005, which is a continuation of International Application PCT/JP03/14203, filed Nov. 7, 2003, which claims priority to Japanese Patent Application No. 2002-324177 filed Nov. 7, 2002.

TECHNICAL FILED

The present invention relates to a magnetic material for collecting magnetic particles, a method of collecting magnetic particles using the magnetic material, and an apparatus for using the magnetic material. The present invention can be used in analyses using magnetic particles, such as an immunoassay.

BACKGROUND ART

In recent years, many techniques that involve use of micro-magnetic particles as carriers and various reactions in solutions have been developed. Various techniques using magnetic particles, for example, an immunoassay (see, for example, J. Immnunol. Methods, 218:1-2, 1-8, Sep. 1 (1998)), a method of extracting and analyzing nucleic acids (see, for example, Biotechniques, 13:1, 124-31, July (1992)), a method of analyzing proteins or ligands, chemical reactions such as combinatorial chemistry, have been developed and extensively used.

For example, among various immunoassays that are extensively used as methods of detecting various diseases in early stages and methods of detecting trace amounts of substances, techniques that involve use of magnetic particles having carried thereon antigens or antibodies are highly evaluated since the techniques give high sensitivities and allow simple operation of B/F separation and so on. "B/F separation" means a step of separating an antigen-antibody reaction product from an unreacted substance by discarding the reaction mixture containing the unreacted substance from a reaction vessel such as a reaction tube or wells of a microtiter plate and repeating a washing operation that includes supplying and discarding a washing solution. When magnetic particles having carried thereon an antigen or an antibody are used, the magnetic particles and a sample are mixed to perform an antigen-antibody reaction, and then B/F separation including a step of collecting the magnetic particles that contain the generated immune complex and a step of separating and washing unreacted antigen or antibody can be performed easily and quickly using magnetic force.

Specifically, a method that involves contacting the magnetic material with a reaction vessel or the like that is in a state of stand still, such as a reaction tube or wells of a microtiter plate, and collecting magnetic particles (see, for example, JP 3-144367 A); a method which involves collecting magnetic particles by contacting a magnetic material with a tip, a stainless steel pipe, or a flexible tube used as a flow line for sucking/discharging liquid from/into a vessel (see, for example, JP 3115501 B); and many other reports have been made.

However, for these methods, it is an important problem to improve the recovery rate (collection efficiency) of the magnetic particles. Although the micro-magnetic particles are useful for performing various reactions at a high efficiency, they tend to float in the solution, which tends to lead to a reduced recovery rate. When the recovery rate decreases, the magnetic particles may flow outward in the processes of washing, separation and so on to cause an error. This may reduce the reliability of measured values. However, when the washing is insufficient with a view to preventing the magnetic particles from flowing outward, complete separation cannot be attained. In addition, samples after separation, for example, pretreated samples are used, contamination may occur. In particular, in the case of the immunoassays, the B/F separation is performed a plurality of times and if the outward flow of the magnetic particles or errors occur, the measured values are greatly influenced.

To solve those problems, for example, a method that involves settling the magnetic particles over a long time until all the magnetic particles are collected without fail has been tried. Surely, this method allows one to collect the magnetic particles in a relatively short time when a reaction vessel in which the reaction mixture stands still, such as a reaction tube or a microtiter plate, is used. However, when the reaction mixture flows as in the case of a flow line that sucks liquid from the vessel and discharges the liquid, it is difficult to improve the recovery rate. In addition, the above-mentioned method requires a long time for measurement, so the method is unsuitable for clinical tests or the like for which rapid measurements are required.

On the other hand, a method of enhancing the magnetic force using electromagnets or permanent magnets with enlarged sizes that are employed as a magnetic material for collecting the magnetic particles has been tried. However, this method is not practically acceptable since it has a problem, for example, that a large apparatus is necessary.

As described above, it is hardly to say that a method of collecting magnetic particles with ease and in a high efficiency, which method exhibits a high reproducibility even in the immunoassays that involve a plurality of B/F separation operations, has been already established. Accordingly, development of a magnetic material that is small and can collect magnetic particles in a high efficiency is demanded. In particular, in the field of Point of Care Testing (POCT) and the like that are attached importance in recent years in clinical tests, demanded is an apparatus that is small and easy to handle and with which medical physicians and nurses can perform tests quickly. Accordingly, down-sizing of the apparatus is essential. In addition, it is required that the apparatus used in the field of POCT is adapted to use whole blood immediately after taking the blood sample as it is to achieve tests quickly. However, when the whole blood containing a lot of contaminant proteins is used as a sample, the magnetic particles tend to aggregate, which leads to a decrease in the recovery rate of the magnetic particles. Accordingly, it is keenly demanded to perform B/F separation at a high recovery rate using strong magnetic material.

DISCLOSURE OF THE INVENTION

The present invention has been made to provide a magnetic material for collecting magnetic particles that collects the magnetic particles with ease and at a high efficiency, a method of collecting magnetic particles using the magnetic material, and an apparatus having provided therewith the magnetic material.

The inventors of the present invention have made extensive study to achieve the above-mentioned problems. As a result, the inventors have found that a magnetic material capable of collecting magnetic particles efficiently can be produced by assembling a plurality of magnets in parallel to the direction of magnetization in such a manner that the south and north poles of adjacent magnets alternately reversed. The present invention has been accomplished based on these findings.

That is, according to the present invention, there is provided:

(1) a magnetic material for collecting magnetic particles, the magnetic material including a plurality of magnets that are arranged in contact one with another in parallel to a direction of magnetization in such a manner that south and north poles of adjacent magnets are reversed alternately.

Further, according to another aspect of the present invention, there are provided:

(2) a magnetic material for collecting magnetic particles, having at least one peak of a magnetic force in a magnetic pole surface, wherein the peak magnetic force is 600 gausses or more;

(3) a method of collecting magnetic particles by adsorbing and holding the magnetic particles in a liquid on a wall surface by a magnetic force and then making the magnetic particles unaffected by the magnetic force to release the magnetic particles, the method including generating the magnetic force from a magnetic material for collecting the magnetic particles, in which the magnetic material includes a plurality of magnets arranged in contact one with another in parallel to a direction of magnetization in such a manner that south and north poles of adjacent magnets are reversed alternately;

(4) the method according to (3) described above, in which the wall surface is an inner wall surface of a liquid suction line of a dispenser that sucks a liquid from a vessel and discharges the liquid;

(5) the method according to (3) or (4) described above, in which the magnetic particles are used for performing an immunoassay;

(6) a method of collecting magnetic particles by adsorbing and holding the magnetic particles in a liquid on a wall surface by a magnetic force and then making the magnetic particles unaffected by the magnetic force to release the magnetic particles, the method including generating the magnetic force from a magnetic material for collecting the magnetic particles, wherein the magnetic material has at least one peak of the magnetic force in a magnetic pole surface, and the peak magnetic force is 600 gausses or more;

(7) the method according to (6) described above, in which the wall surface is an inner wall surface of a liquid suction line of a dispenser that sucks a liquid from a vessel and discharges the liquid;

(8) the method according to (6) or (7) described above, in which the magnetic particles are used for performing an immunoassay;

(9) a method of an immunoassay for a substance to be tested which is present in a sample, comprising:

(a) a first reaction step of adding, to a sample, magnetic particles having carried thereon a first substance capable of specifically binding to a substance to be tested contained in the sample to cause reaction, (b) a first separation step of separating a first reaction product formed in the first reaction step from the reaction system, (c) a second reaction step of adding a second substance capable of specifically binding to the separated first reaction product to cause reaction to form a second reaction product in the reaction system, (d) a second separation step of separating the second reaction product formed in the second reaction step from the reaction system, and (e) a measuring step of measuring an amount of the separated second reaction product, in which the separation of the first and second reaction products from the reaction system is performed by using a magnetic material for collecting magnetic particles, the magnetic material including a plurality of magnets arranged in contact one with another in parallel to a direction of magnetization in such a manner that south and north poles of adjacent magnets are reversed alternately;

(10) the method according to (9) described above, in which the measurement of the amount of the second reaction product is performed by a chemiluminescent method or a fluorescent method;

(11) a method of an immunoassay for a substance to be tested which is present in a sample, comprising:

(a) a first reaction step of adding, to a sample, magnetic particles having carried thereon a first substance capable of specifically binding to a substance to be tested contained in the sample to cause reaction, (b) a first separation step of separating a first reaction product formed in the first reaction step from the reaction system, (c) a second reaction step of adding a second substance capable of specifically binding to the separated first reaction product to cause reaction to form a second reaction product in the reaction system, (d) a second separation step of separating the second reaction product formed in the second reaction step from the reaction system, and (e) a measuring step of measuring an amount of the separated second reaction product, wherein the separation of the first and second reaction products from the reaction system is performed by using a magnetic material having at least one peak of a magnetic force in a magnetic pole surface, the magnetic force being at 600 gausses or more; (12) the method according to (11) described above, in which the measurement of the amount of the second reaction product is performed by a chemiluminescent method or a fluorescent method;

(13) an apparatus comprising a dispenser having a liquid suction line that sucks a liquid from a vessel and discharges the liquid, and a magnetic material provided in the liquid suction line, in which the apparatus is configured to be controlled in such a manner that magnetic particles in the liquid sucked by the liquid suction line are adsorbed and held on an inner wall surface of the liquid suction line by a magnetic force of the magnetic material, and then the magnetic particles are made unaffected by the magnetic force of the magnetic material to release the magnetic particles from the liquid suction line and discharged together with the liquid to outside the liquid suction line, and in which the magnetic material includes a plurality of magnets that are arranged in contact one with another in parallel to a direction of magnetization in such a manner that south and north poles of adjacent magnets are reversed alternately;

(14) an apparatus comprising a dispenser having a liquid suction line that sucks a liquid from a vessel and discharges the liquid, and a magnetic material provided in the liquid suction line, in which the apparatus is configured to be controlled in such a manner that magnetic particles in the liquid sucked by the liquid suction line are adsorbed and held on an inner wall surface of the liquid suction line by a magnetic force of the magnetic material, and then the magnetic particles are made unaffected by the magnetic force of the magnetic material to release the magnetic particles from the liquid suction line and discharged together with the liquid to outside the liquid suction line, and in which the magnetic material has at least one peak of the magnetic force in a magnetic pole surface and the peak magnetic force is 600 gausses or more.

BEST MODE FOR CARRYING OUT THE INVENTION

Hereinafter, the present invention will be explained in more detail.

1. Magnetic Material for Collecting Magnetic Particles According to the Present Invention The magnetic material for collecting magnetic particles according to the present invention includes a plurality of magnets arranged in such a manner that adjacent magnets contact each other. The magnets in the magnetic material of the present invention has such a feature that they are arranged in parallel to the direction of magnetization in such a manner that the south and north poles of the adjacent magnetic poles are reversed alternately (hereinafter, this being also referred to as "layered"). As used herein, the term "parallel" does not mean that the direction of magnetization of each magnet constituting the magnetic material is the same. The term "parallel" also includes the case in which the direction of magnetization of one magnet is opposite to the direction of magnetization of another magnet.

Generally, the magnetic force of a magnet is strong at the end portion of a side from which the magnet generates magnetic force (a side vertical to the direction of magnetization of the magnet constituting the magnetic material: hereinafter, this being also referred to as a "magnetic pole surface"), and weak in the central portion of the side. Therefore, when, for example, a magnetic material composed of a single magnet (hereinafter, this being also referred to as a "single magnet-magnetic material") is used, a strong magnetic force is obtained only at the end portion of the magnetic material even if a large magnet is used. Strong magnetic force therefore cannot be obtained over the entire pole surface of the magnet. This makes collection of the magnetic particles inefficient.

In contrast, in the case of the magnetic material of the present invention, a plurality of magnets are arranged in parallel to the direction of magnetization in such a manner that the south and north poles of adjacent magnets are reversed alternately. Thus, it is found that strong magnetic force can be obtained at the sites where the magnets contact each other in the magnetic material (hereinafter, this being also referred to as "layered portion") and the magnetic force is weak in the central portion of each magnet. That is, in the single magnet-magnetic material, a strong magnetic force can be obtained only at the end portion of the magnet in a pole surface having a certain fixed area. In contrast, the magnetic material of the present invention has such a feature that strong magnetic force is obtained at a plurality of sites of the pole surface of the magnetic material since a plurality of the magnets are layered to constitute the magnetic material. In other words, the magnetic material of the present invention has at least one peak of magnetic force in the pole surface. "Having a peak" means that the magnetic force at a point in the magnetic pole surface is greater than the magnetic forces at points on both sides of the above-mentioned point in the cross-sectional direction of the magnets, with this point being called a "peak".

For example, the single magnet-magnetic material has sites where strong magnets are obtained only on both ends of the magnetic pole surface. In the case of the magnetic material having layered two magnets, strong magnetic forces are obtained (the magnetic material has peaks) at one layered portion as well as at the both ends. In the case of the magnetic material having layered three magnets, strong magnetic forces are obtained (the magnetic material has peaks) at two layered portions as well as at the both ends.

Generally, the distance in which the magnetic lines reach (range of magnetic field) increases with an increasing size of the magnet. Therefore, it has been conceived that use of a strong magnetic force from a large magnet would increase the effect also in, for example, collecting the magnetic particles. However, recent developments of the technology have allowed fine disposable tips and the like to be used as a flow line that sucks liquid from a vessel and discharges the liquid (hereinafter, this being also referred to as a "liquid suction line") and simply applying a large magnet to such a flow line makes the range in which the magnetic lines reach too wide to centralize the magnetic lines within the internal diameter portions of the tips or the like. Accordingly, there is a problem that stray magnetic field expands.

In contrast, the magnetic material of the present invention includes a plurality of magnets combined with each other, so each magnet can have an appropriately small size. This makes the distance in which the magnet lines reach short and the magnet lines accumulate near the magnetic pole surface, resulting in a decreased stray magnetic field. Therefore, for example, when the magnetic material of the present invention is used as a magnetic material for collecting magnetic particles and contacted to a liquid suction line having a thin flow path, the magnetic particles can be collected efficiently.

By the above-mentioned two great features, the magnetic material of the present invention can very efficiently collect magnet particles on the inner wall of the liquid suction line or vessel, and hence is very suitable as a magnetic material for collecting magnetic particles.

Any magnet having an S pole (south pole) and an N pole (north pole) and capable of generating magnetic force that can collect magnetic particles may be used. Examples of the magnets include permanent magnets and electromagnets. Permanent magnets are preferably used in view of intensity and stability of the generated magnetic field and because no power source is necessary. Examples of the permanent magnet include those obtained by molding suitable magnetic materials, such as Alnico, barium ferrite, neodymium, and samarium cobalt, into any desired shapes, such as rod, plate, cube, disk, and horseshoe arch, and magnetizing the molded magnetic materials. The rod-shaped permanent magnet preferably has a rectangular cross-section. Among the above-mentioned magnets, a neodymium magnet molded into a rod or a plate is preferably used.

The magnetic material of the present invention can be produced by arranging a plurality of the above-mentioned magnets in contact with each other in parallel to the direction of magnetization in such a manner that the south and north poles of adjacent magnetic poles are reversed alternately. Even when a space is present between the magnets, the magnets are considered to substantially contact with each other as long as the magnetic material is constituted integrally and the desired magnetic force is sufficiently obtained. The term "in contact" in the present invention includes the case in which the magnets substantially contact each other in this manner. However, it is preferable that no space is present between the magnets.

At least two magnets, preferably at least three magnets, are used in combination. The upper limit of the number of the magnets depends on the size of the magnet used and the designed size (outer size) of the magnetic material of the present invention to be produced from a plurality of the magnets. The sizes of the magnets may be the same or different from each other. It is preferable that the magnets have the same size.

For example, when the each of magnets is too small, the magnetic force generated is weak and the efficiency of collecting the magnetic particles may decrease. It is preferable to select magnets having a suitable size in accordance with the outer size of the magnetic material to be produced in such a manner that the magnetic force at the site where the magnetic particles are collected is maximum. The preferable number and size of magnets may be determined by measuring the magnetic force at the site where the magnetic material contacts by the technique explained later, or actually obtaining the recovery rate of the magnetic particles, and confirming that the magnetic force of the magnetic material is sufficient for collecting the magnetic particles. The outer size may be determined in view of the size of the reaction vessel or the like to which the magnetic material is contacted and the specification of the apparatus in which the magnetic material is arranged. It may be sufficient to take into consideration, for example, that the outer size of the magnetic material must not be too large with respect to the apparatus, and that the portions of the apparatus that are susceptible to the influence of magnetic force, such as photomultipliers, must not be influenced by the magnetic force.

More particularly, for example, when the magnetic material is used as arranged in an automatic measuring apparatus having a liquid suction line ("SX-6G", manufactured by Precision System Science Corporation, etc.), the outer size of the magnetic material may be determined depending on the length, inner diameter, wall thickness, material and the like of the tips used as the line. The length of face (magnetic pole surface) of a single magnet that contacts the line is determined depending on the wall thickness and so on. It is important to use a magnetic material that generates magnetic lines between the adjacent magnets appropriately reach the moving line of the magnetic particles. More particularly, when tips having a wall thickness of 0.75 mm are used, the longitudinal length of a single magnet (longitudinal length of the magnet in the direction of lamination) is preferably 3 mm or more. In the case of vessels that are used in a state of stand still such as a reaction tube and a microtiter plate, the longitudinal length of the magnet may be determined depending on, for example, the length, inner diameter, wall thickness, and material of the reaction tube, or the size of the microtiter plate and the size of wells thereon.

Hereinafter, taking an example of the magnetic material used as arranged in a small-size automatic measuring apparatus such as "SX-6G" manufactured by Precision System Science Corporation, the magnetic material of the present invention and the method of selecting magnets for producing the magnetic material are explained in more detail. In the apparatus, disposable tips having an inner diameter of about 2 to 3 mm and a wall thickness of about 0.5 to 1 mm are arranged as a liquid suction line for sucking and discharging a liquid. For example, polypropylene-made disposable tips having an inner diameter of 2.25 mm and a wall thickness of 0.75 mm are preferable used.

The magnetic material for collecting magnetic particles that is used in contact with the liquid suction line as described above has a size of, for example, 50 mm or less, preferably 20 mm or less in longitudinal length (direction of lamination) and 20 mm or less, preferably 15 mm or less in transverse length (direction of magnetization). The magnetic material has a width of 10 mm or less, preferably 5 mm or less. The lower limits of the size may be any desired size so far as the object of collecting the magnetic particles is achieved. The number of magnets to be layered is preferably 2 to 4, particularly preferably 3 when producing a magnetic material having an outer size of, for example, 15 mm in longitudinal length×14 mm in transversal length×4 mm in width. That is, the longitudinal length of one magnet is suitably about 3.75 to 7.5 mm.

The size of each magnet that constitutes the magnetic material of the present invention can be determined reliably, for example, by measuring the magnetic force on the inner wall surface of the liquid suction line, which is a site where the magnetic particles are adsorbed to confirm that the measured magnetic force is sufficient for adsorbing the magnetic particles. Also, a method that involves actually measuring the recovery rate (collection efficiency) of the magnetic particles to confirm that the measured recovery rate is preferably 80% or more, particularly preferably 90% or more is preferably used.

Examples of the method of measuring the magnetic force on the inner wall surface includes a method of actually measuring the magnetic force exerted on the inner wall surface of the liquid suction line using a commonly used magnetic force measuring apparatus, such as a handy gauss meter (MODEL 4048: manufactured by F. W. BELL). More particularly, for example, a measuring probe (for example, in the case of the above-mentioned measuring apparatus, T-4048-001 (manufactured by F. W. BELL)) is set near the pole surface of the magnetic material and the magnetic force is measured. In this case, the probe is set advantageously at a small distance from the magnetic pole surface taking into consideration that the tip has actually a wall thickness. Also, the magnetic force may be measured, for example, by actually contacting the magnetic material with the outer wall surface of the tip and setting the probe on the inner wall surface to measure the magnetic force on the inner wall surface of the tip.

As described previously, the pole surface of the magnetic material of the present invention has a strong peak at the site where the magnets contact each other (layered portion) and a weak magnetic force in the central portion of each magnet. That is, when the magnetic material of the present invention is produced, it is preferable that an indicator is adopted that a sufficient magnetic force can be obtained not only at the end portions but also at each layered portion. The magnetic material of the present invention preferably includes a plurality of layered portions and has a sufficient size for the magnetic force in each layered portion to collect the magnetic particles. The term "sufficient magnetic force at each layered portion" means, for example, 600 gausses or more, preferably 800 gausses or more, more preferably 1,000 gausses or more.

Therefore, when the magnetic force of the magnetic material of the present invention is measured, it is preferable that the measurement is performed at a plurality of sites on the magnetic pole surface to confirm that a sufficient magnetic force can be obtained over the plurality of the sites. The probe may be set either vertically or in parallel to the magnetic pole surface so far as the measurement is performed according to a predetermined technique and the measured values can be compared. However, since the measuring portion of the probe generally has a certain area and it is difficult to measure the magnetic force at a single point. However, by setting the probe vertically with respect to the magnetic pole surface and measuring the magnetic force at a plurality of points on the magnetic pole surface, accurate comparisons can be made. In particular, it is preferable that the magnetic force at the layered portions is measured. More preferably, continuous measurements are made at a plurality of points including those in the layered portions and the number of peaks of the magnetic force and the intensity of the magnetic force are analyzed.

When judgment is made using the recovery rate of the magnetic particles as an indicator, the recovery of the magnetic particles can be obtained by actually providing a commercially available magnetic particle dispersion in an automatic measuring apparatus having arranged therein the magnetic material of the present invention and performing experiments in the same manner as the target measuring method. Examples of the magnetic particles include HTLV-1 magnetic particle reagent Lumipulse HTLV-1 (manufactured by FUJIREBIO, INC.), TP-N magnetic particle reagent Lumipulse II TP-N (manufactured by FUJIREBIO, INC.), and magnetic particle RP-M1 (manufactured by Rohne-Poulenc).

The method of producing the magnetic material of the present invention by contacting a plurality of magnets in parallel each other may utilize the holding powers of the magnets in binding the magnets to each other since the magnets are adjacently arranged with the south and north magnetic poles being reversed alternately, or may utilize bonding adhesive or the like. As described above, so far as the magnetic material has a sufficient magnetic force, a space may be present between adjacent magnets.

2. Method of Collecting Magnetic Particles Using Magnetic Material of the Present Invention The method of collecting magnetic particles of the present invention involves adsorbing and holding the magnetic particles in a liquid on the wall surface by the magnetic force and then making the magnetic particles unaffected by the magnetic force to release the magnetic particles and is characterized in that the magnetic force is generated by the above-mentioned magnetic material of the present invention.

The magnetic material used in the present invention is the above-mentioned magnetic material of the present invention. The above-mentioned magnetic material can generate strong magnetic force in the layered portion of the magnets and has a feature that the magnetic lines accumulate near the magnetic material, so the stray magnetic field decreases, and hence the magnetic force is increased in the side (magentic pole surface) vertical to the direction of magnetization of the magnets constituting the magnetic material. Accordingly, the magnetic particles can be collected effectively using the magnetic pole surface.

The term "wall surface" as used herein means an inner wall surface and the like of a reaction vessel such as a reaction tube or wells of a microtiter plate, and of the liquid suction line of a dispenser that sucks liquid from a vessel and discharges the liquid. In the present invention, it is preferable that the wall surface is the inner wall surface of the above-mentioned liquid suction line. By contacting the magnetic material of the present invention with the outer wall surface of, for example, the tips, stainless steel pipes, and flexible tubes that are used as the liquid suction line, the magnetic particles can effectively be adsorbed and held on the inner surface of the site where the magnetic material is contacted (hereinafter, this being also referred to as "magnetic force site"). Also, by releasing the magnetic particles from the magnetic force site to make the magnetic particles unaffected by the magnetic force of the magnetic particles, the magnetic particles can be simply and easily released from the inner wall surface. Conventional technique has a problem that the magnetic particles tend to be lost. However, with the magnetic material of the present invention, high recovery rates are achieved, which solves the problem.

To make the magnetic particles unaffected by the magnetic force, the magnetic material is held off the wall surface when the magnetic material is a permanent magnet and when the magnetic material is an electromagnet, the object is achieved by the same method as described above or by stopping the application of current to the electromagnet in the same manner as described above.

Any magnetic particles may be used so far as the magnetic particles have properties of being collected under the influence of magnetic force generated by the magnetic material. The diameter is not limited. The shape of the magnetic particles is not limited to spherical and those magnetic particles that have a suitable material, coating, and size depending on the objective measurement, analysis, reaction and so on may be selected and used.

More particularly, for example, when an immunoassay is performed, magnetic particles made of metals such as triiron tetraoxide ($Fe_3O_4$), diiron trioxide ($Fe_2O_3$), various types of ferrites, iron, manganese, nickel, cobalt, and chromium, alloys of cobalt, nickel, and manganese are preferably used. These magnetic particles may be prepared as included in latex of a polymer such as polystyrene, gelatin, liposomes, or as immobilized on the surface thereof. The shape of the magnetic particles is preferably spherical. The particle size of the magnetic particles may be any particle size so far as the B/F separation can be performed with a high accuracy using the magnetic material of the present invention. However, if the particle size is too small, the efficiency of the separation is poor while the magnetic particles tend to precipitate if the particle size is too large. More particularly, for example, the lower limit of the particle size is 0.05 μm, preferably 0.1 μm while the upper limit of the particle size is 10 μm, preferably 4 μm, more preferably 2 μm. The ranges of the particle size are selected from combinations of the upper and lower limits. Specific example of the particle size is usually from 0.05 to 10 μm, preferably from 0.05 to 4 μm, more preferably 0.1 to 2 μm.

An antigen or an antibody is carried on the magnetic particles by a method that is commonly used and known per se and the resultant is used in the immunoassay. Examples of the method of carrying an antigen or an antibody on the magnetic particles include a physical adsorption method and a chemical binding method. The amount of adsorption, the kind of the solution in which the magnetic particles are suspended, the concentration of the magnetic particles in the solution, and so on may be appropriately selected depending on the magnetic particles used, antigen or antibody, target of measurement, sample, and so on.

Most of the magnetic particles as described above and the magnetic particles that carry any antigen or antibody are offered commercially as magnetic particles or reagents and are readily available.

For example, those magnetic particles used for extracting and analyzing nucleic acids may be any magnetic particles so far as they can be mixed with a solution containing a nucleic acid and subjected to a reaction as necessary to have the nucleic acid attached to the surface thereof.

The site and method of collecting the magnetic particles may be performed according to the method of collecting the magnetic particles by a magnetic material that is known per se and commonly used. As described above, it is preferable that the magnetic material is used in such a manner that the side (magnetic pole surface) which is vertical to the direction of magnetization of the magnets constituting the magnetic material of the present invention contacts the outer wall surface of the reactor or the like presented for the target measurement, analysis, and reaction. More particularly, for example, when the magnetic particles are collected in a vessel that is used in a state of stand still, such as a reaction tube or a microtiter plate, the magnetic material of the present invention can be used by contacting the magnetic material with the reaction tube or wells of the microtiter plate at the side or bottom thereof. When the magnetic particles are collected in tips, stainless steel pipe, a flexible tube, or the like used as the liquid suction line of a dispenser arranged in the apparatus performing measurement, analyses, and reactions by using the magnetic particles, the magnetic material of the present invention can be used by contacting it with the side of the tip, stainless steel pipe, or flexible tube. Among those, the method of the present invention is used particularly advantageously in an automatic measuring apparatus in which a liquid suction line is arranged.

The method of the present invention can be applied to various measurements, analyses, reactions and so on that are performed using magnetic particles. The substances to be tested, which are targets of measurement include, for example, immunological substances, biological substances, molecular substances, and so on such as antigens, antibodies, proteins, ligands, enzymes, substrates, DNAs, vector DNAs, RNAs, and plasmids. For the qualitative/quantitative determination of these substances, various kinds of labeled substances used for isotopes, enzymes, chemiluminescence, fluorescence, electrochemiluminescence, and so on are employed. The measuring method and apparatus that can be used may be those known per se and commonly used.

More particularly, the method of the present invention is advantageously used in, for example, an immunoassay, method of extracting and analyzing nucleic acids, method of analyzing proteins/ligands, combinatorial chemistry, chemical reactions such as pretreatments of various samples. For example, in an immunoassay, the method of collecting the magnetic particles according to the present invention is applied to the step of B/F separation. For example, in the method of extracting/analyzing nucleic acids, the method of the present invention is applied to the step of separating/purifying nucleic acids. For example, when the samples from which nucleic acids are extracted are various kinds of cells, the cells are solubilized by a known method to prepare a cell extract solution, which is then mixed with the magnetic particles to adhere the nucleic acid on the surface of the magnetic particles. By collecting the magnetic particles having adhered the nucleic acid thereon by the method of collecting the magnetic particles of the present invention, the nucleic acid can simply and easily be separated/purified from the cell extract solution that contains contaminants in large amounts. In the case of chemical reactions such as combinatorial chemistry, the method of the present invention is applied to the step of separating/purifying the product synthesized by the chemical reaction.

Among the various methods, the method of collecting the magnetic particles of the present invention is applied to particularly preferably B/F separation in an immunoassays.

3. Immunoassay of the Present Invention

The immunoassay of the present invention is featured by using the above-mentioned magnetic material for collecting the magnetic particles in B/F separation.

More particularly, for example, in a method that includes: (a) a first reaction step of adding, to a sample from a patient, magnetic particles having carried thereon a first substance capable of specifically binding to a substance to be tested contained in the sample to cause reaction; (b) a first separation step of separating a first reaction product formed in the first reaction step from the reaction system; (c) a second reaction step of adding a second substance capable of specifically binding to the separated first reaction product to cause reaction to form a second reaction product in the reaction system; (d) a second separation step of separating the second reaction product formed in the second reaction step from the reaction system; and (e) a measuring step of measuring the amount of the separated second reaction product, the separation (B/F separation) of the first and second reaction products from the reaction system in the steps (b) and (d) above is performed by the method of collecting magnetic particles using the magnetic material of the present invention. The immunoassay can also be performed using an automatic immunoassay apparatus.

The first and second substances are an antigen and an antibody and the reaction product means an immune complex. The sample contains a substance to be tested that specifically reacts with the first substance, for example, a biological sample, environmental sample, a food sample, and so on. The biological samples are samples obtained from living organisms, for example humans, preferably samples obtained from patients. The samples obtained from patients may be any samples from the patients requiring measurements or analyses, for example, body fluids such as blood, blood serum, plasma, urine, and saliva, various cells, tissues or extracted solutions therefrom. The environmental samples include waters of rivers, seas, lakes, or the like and soils and so on.

The measurement of the amount of the reaction product can be performed by a method known per se and is used commonly. For example, it is preferable to label the first substance or the second substance with a labeling substance and measure the amount of the labeling substance contained in the reaction product separated from the reaction system. More particularly, in the case of enzyme immunoassay, the assay can be performed by reacting an enzyme which labeled a secondary antibody with its substrate and measuring the amount of the reaction product by an optical technique or the like. In the case of chemiluminescent immunoassay, the amount of luminescence by a luminescent reaction system is measured. In the case of fluorescent antibody method, the intensity of fluorescence due to the fluorescent substance is measured. In the radioimmunoassay, the amount of radio activity due to the radioactive substance is measured. Examples of the labeling substance include enzymes such as peroxidase, alkaline phosphatase, β-D-galactosidase, and glucose oxidase; fluorescent substances such as fluorescein isothiocyanate and rare earth metal chelates; radioisotopes such as $^3H$, $^{14}C$, and $^{125}I$; and chemiluninescent substances. The enzymes and chemiluminescent substances cannot give signals that can be measured by themselves and hence suitable substrates that correspond to them are selected and used. Also, biotin, avidin, and so on may be used in these reactions.

For example, enzymes are used in enzyme chemiluminescent enzyme immunoassay (CLEIA). Examples of such enzymes include alkaline phosphatase, peroxidase, galactosidase, and glucose oxidase. The substrates that can be used therefor are those corresponding thereto. For example, adamantylmethoxyphenylphosphoryldioxetane (AMPPD), and 2-chloro-5-(4-methoxyspiro{1,2-dioxetane-3,2'-(5'-chloro)-tricyclo[3.3.1.1$^{3,7}$]decan}-4-yl)-1-phenylphosphate disodium (trade name "CDP-STAR": manufactured by Tropix), which are chemiluminescent substrates derived from 1,2-dioxetane, can be used for alkaline phosphatase, luminol/peroxide can be used for peroxidase, and adamantylmethoxyphenyl-β-D-galactosyldioxetane (AMPGD) can be used for galactosidase. In the immunoassay to which the method of the present invention is applied, the detection method using the enzyme chemiluminescent immunoassay is preferably used and alkaline phosphatase is particularly preferably used as the labeling substance and chemiluminescent substrates derived from 1,2-dioxetane (for example, "CDP-STAR" manufactured by Tropix) are particularly preferably used as substrates. Also, a fluorescent method is preferably used.

Hereinafter, the present invention will be explained in more detail taking an example of the case of incorporating the magnetic material of the present invention in an automatic immunoassay apparatus and performing immunoassay using magnetic particles. Taking an example of an apparatus for performing immunoassay using magnetic particles, which apparatus is provided with a tip as a liquid suction line of a dispenser and is capable of performing simple measurement using an automatic measuring cartridge and the like connected with a plurality of reactors (see, for example, JP 3115501 B), the method of the present invention is explained step after step.

(1) The magnetic material of the present invention as a magnetic material for collecting magnetic particles is incorporated in an automatic immunoassay apparatus that can perform immunoassay using the magnetic particles.

(2) A solution containing magnetic particles having carried thereon an antibody when the target test substance is an antigen or an antigen when the target test substance is an antibody is prepared.

(3) A sample solution obtained from a patient, a sample diluting solution, a solution containing magnetic particles, a washing solution for B/F separation, a labeled antibody solution, a substrate solution, and so on are filled in the automatic measuring cartridge, and a cartridge is set in the apparatus.

(4) The apparatus in which the magnetic material of the present invention is incorporated in (1) described above is operated to perform measurements first by mixing a sample solution adjusted to an arbitrary dilution factor using a diluting solution, with the solution containing the magnetic particles to perform a first antigen-antibody reaction.

(5) Then, B/F separation to remove unreacted substances is performed First, the reaction mixture is sucked through a tip set as a liquid suction line, at the same time, the magnetic material of the present invention is contacted to the outer wall surface of the tip. Preferably, the suction and discharging of the solution are repeated several times in a state where the magnetic material is still in contact to adsorb and hold the magnetic particles sufficiently on the inner wall surface of the magnetic force site. Next, the solution is discharged in a state where the magnetic particles are adsorbed and held on the inner wall surface of the tip and then the washing solution for B/F separation filled in a separate reactor is sucked and discharged to perform washing.

(6) After releasing the magnetic material of the present invention from the outer wall surface of the tip to remove the influence of the magnetic force, the labeled antibody solution, for example, alkaline phosphatase (ALP)-labeled secondary antibody solution is sucked and discharged to disperse the magnetic particles adsorbed and held on the inner wall surface of the tip in (5) described above, and allow to bind to the test substance specifically to perform a second antigen-antibody reaction to produce an immune complex.

(7) A second B/F separation is performed in the same manner as in (5) described above to remove and wash unreacted labeled antibody (ALP-labeled secondary antibody).

(8) The amount of the labeling substance contained in the immune complex produced in (6) described above is measured. When ALP is used as the labeling substance, a chemiluminescent substance (for example, "CDP-STAR", manufactured by Tropix) derived from 1,2-dioxetane is reacted to ALP and the signal generated is measured using a photomultiplier. Based on the measured values, the amount of the test substance contained in the sample from the patient can be obtained.

4. Apparatus for Using Magnetic Material of the Present Invention

The magnetic material of the present invention and the method of collecting magnetic particles using the magnetic material are very useful for use in a measuring apparatus since the magnetic material has the property of generating a strong magnetic force as compared with a single magnet-magnetic material having the same size at a specific magnetic force site. In particular, the magnetic material of the present invention can be used particularly advantageously in an apparatus that is required to be provided with a smaller and strong magnetic material, such as an apparatus in which the size (outer size) of the magnetic material is limited to a certain extent, an apparatus that is required to be down-sized or the like.

The magnetic material and the apparatus that has incorporated therein the magnetic material of the present invention may be any apparatus for performing various measurements, analyses, reactions, and so on using magnetic particles as described above. Among those, an automatic immunoassay apparatus having incorporated therein the magnetic material of the present invention is particularly preferable. An apparatus for immunoassay entirely or partly automated and known per se or a combination of such automatic immunoassay apparatuses can be used as the automatic immunoassay apparatus. It is particularly preferable that in such apparatuses the magnetic material of the present invention is used as arranged in a liquid suction line of a dispenser sucking the liquid from a vessel and discharging the liquid.

That is, according to the present invention, there is provided an apparatus that includes a dispenser having a liquid suction line sucking a liquid from a vessel and discharging the liquid, and a magnetic material provided in the liquid suction line, and that is configured to be controlled in such a manner that magnetic particles in the liquid sucked by the liquid suction line are adsorbed and held on an inner wall surface of the liquid suction line by a magnetic force of the magnetic material, and then the magnetic particles are made unaffected by the magnetic force of the magnetic material to release the magnetic particles from the liquid suction line and discharged together with the liquid to outside the liquid suction line, and wherein the magnetic material comprises a plurality of magnets that are arranged in contact one with another in parallel to a direction of magnetization in such a manner that south and north poles of adjacent magnets are reversed alternately.

Further, there is provided the above-mentioned apparatus wherein the apparatus includes a dispenser having a liquid suction line sucking a liquid from a vessel and discharging the liquid, and a magnetic material arranged in the liquid suction line, and the apparatus is configured to be controlled in such a manner that magnetic particles in the liquid sucked by the liquid suction line are adsorbed and held on an inner wall surface of the liquid suction line by a magnetic force of the magnetic material, and then the magnetic particles are made unaffected by the magnetic force of the magnetic material to release the magnetic particles from the liquid suction line and discharged together with the liquid to outside the liquid suction line, and wherein the magnetic material has at least one peak of the magnetic force in a pole surface of the magnetic material and the peak magnetic force is 600 gausses or more.

The apparatus provided with a liquid suction line performs the collection of magnetic particles from the liquid containing the magnetic particles not on a vessel containing the liquid, but in the liquid suction line of the dispenser sucking and discharging the liquid and is featured in that the magnetic particles are adsorbed and held substantially completely in a short time by utilizing the magnetic force of the magnetic material arranged on the side of sucking and discharging system of a tip used as the liquid suction line to thereby realize drastic improvement in precision of measurement. When a disposable tip or the like is used as the liquid suction line, cross-contamination between the reagents or between the samples can completely be prevented, and the apparatus can readily handle various test methods in various reaction steps and process steps, thereby enabling multi-item measurements. In addition, the apparatus of the present invention has epoch-making effects that the apparatus using the magnetic particles can be made simplified, easy to handle, and versatile and can be produced at low cost. However, in such apparatuses, since the site at which the magnetic material is acted is not a vessel containing a liquid but a liquid suction line, the liquid is fluid, so it is essential to trap the magnetic particles firmly within a small range. By using the magnetic material of the present invention, deficiency in magnetic force can be solved and high recovery rate can be achieved, resulting in a further improvement in accuracy of measurement.

The above-mentioned magnetic material may be arranged at least one in the liquid suction line according to the aperture of the liquid suction line, the amount and size of the magnetic particles adsorbed and held, and so on. Various embodiments of arrangement can be conceived. For example, the magnetic materials may be arranged along the direction of the flow of the liquid in the liquid suction line, or in a facing state sandwiching the liquid suction line, or radially.

Further, in the present invention, the magnetic material may be arranged on the outside of the above-mentioned liquid suction line or attached to the liquid suction line in a direct contact. When the magnetic material is arranged outside the liquid suction line, the magnetic material is constituted by a permanent magnet and the magnetic material is placed close to the liquid suction line, so the magnetic particles in the liquid sucked in the liquid suction line can be adsorbed and held on the inner wall surface of the liquid suction line. By releasing the magnetic material from the liquid suction line, the magnetic particles can be released form the liquid suction line and discharged together with the liquid to the outside the liquid suction line.

When a tip is used as the liquid suction line, it is desirable that the tip is repeatedly applied only to the same sample in the step in which the sample is treated according to the process based on the predetermined assay. The number of tips used for the same sample may be at least one and the number of tips necessary for the reaction and process steps in various measurements may be used. When the liquid suction line is formed in a nozzle system to and from which the tips are not attached or detached, the inside and outside of the liquid contact portion with which the liquid in the liquid suction line contacts are washed by suction and discharging operations to such an extend that occurrence of cross-contamination can be avoided to perform separation of the magnetic particles from the liquid, stirring, and washing of the magnetic particles.

That is, separation of the liquid and magnetic particles in this apparatus is performed by discharging only the liquid while the magnetic particles are adsorbed and held by the magnetic material. Then, the above-mentioned tip having adsorbed and held the magnetic particles on the inner wall surface thereof by the magnetic force from the magnetic material is inserted into a liquid contained in another vessel and the magnetic particles are made unaffected by the magnetic force from the magnetic material, thus repeating the operations of sucking and discharging the solution. The stirring and washing when the tip is attached to the liquid suction line may be performed by transferring the tip having adsorbed and held the magnetic particles on the inner wall surface to the stirring/washing position and repeating the operations of sucking and discharging the liquid. In this case, the stirring/washing can be performed while adsorbing and holding the magnetic particles on the inner wall surface of the tip or by performing suction/discharging of the liquid at least once in a state where no influence of the magnetic force from the magnetic material is present.

In the above-mentioned apparatus, an automatic measuring cartridge formed so as to have a plurality of container portions (wells) (see, for example, WO 01/84152) is preferably used. By dispensing the sample, reagents, and so on that are necessary for the reaction in advance and packaging them, and configurating the cartridge in such a manner that the magnetic particles adsorbed and held on the inner wall surface of the liquid suction line by the magnetic force of the magnetic material can be transferred as they are to the next well, quick and easy measurements can be made, thus leading to a reduced occurrence of contamination and errors. In this case, each solution to be dispensed may be dispensed in the wells of the cartridge in advance in the same manner as the above-mentioned reagents and the like, or may be provided from a bottle or the like arranged separately in the apparatus. Further, the sample may be dispensed from, for example, the original container for the sample after directly determining the amount thereof. The number of wells in the cartridge may be determined to a necessary number depending on the numbers of the samples, the reagents, the solutions, and the like. The wells may be arranged in a single row or a plurality of rows in the form of a microtiter plate. By forming the wells in this form, multiple items can be measured simultaneously and a multi-sample measurement can be made.

Further, such an automatic measuring apparatus enables to perform measurement and management, analysis, and so on of the results of the measurement more quickly and easily by using an information management technology such as bar code or IC card. For example, in an apparatus that is provided with a bar code in the automatic measuring cartridge and has a function of automatically recognizing the bar code, the data of the patient from whom the sample is acquired and measurement items and so on can be automatically recognized and measurements can be performed without newly inputting/setting measurement conditions such as reaction temperature, photometric conditions. The obtained results of measurements are efficiently grouped and managed based on the data read by the bar code. By using in combination an IC card in which calibration curves and reference values for judgment for respective measurement items are input in advance, the grouped/managed results of measurements can be analyzed and judged.

The above-mentioned apparatus of the present invention includes a magnetic material that is smaller in size and stronger in magnetic force than a single magnet-magnetic material, so the apparatus can be down-sized and reduced in weight and perform immunoassay stably and with a high accuracy. Such a small automatic immune assay apparatus can be used particularly preferably in the field of, for example, Point of Care Testing (POCT) that is highly demanded as emergency tests and tests that can be readily performed by medical physicians and nurses.

EXAMPLES

Hereinafter, the present invention will be explained by examples. However, the present invention should not be considered to be limited to these examples.

Example 1. Preparation of Magnetic Material of the Present Invention

Using commercially available magnets (manufactured by Magna Co., Ltd), a single magnet-magnetic material and the magnetic material of the present invention having arranged a plurality of magnets in contact one with another in parallel to a direction of magnetization in such a manner that south and north poles of adjacent magnets are reversed alternately were provided.

Figure 1:
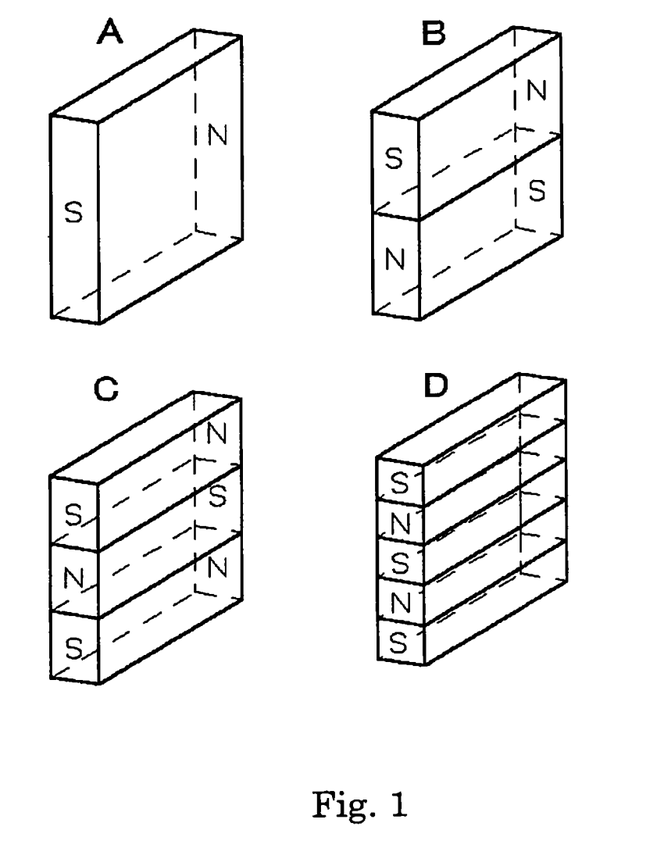
FIG. 1 is a diagram showing configurations of magnetic materials A, B, C, and D, in which A is a single magnet-magnetic material, and B, C, and D are multilayer magnetic materials, respectively, of the present invention.

The single magnet-magnetic material, "magnetic material A", composed of a single magnet having a size of 15 mm in longitudinal length×14 mm in transversal length×4 mm in width (FIG. 1A) was provided.

Then, "magnetic material B" composed of two magnets each having a size of 7.5 mm in longitudinal length×14 mm in transversal length×4 mm in width combined in contact one with another in parallel to a direction of magnetization in such a manner that south and north poles of the adjacent magnets are reversed alternately (FIG. 1B: 15 mm in longitudinal length×14 mm in transversal length×4 mm in width), "magnetic material C" composed of three magnets each having a size of 5 mm in longitudinal length×14 mm in transversal length×4 mm in width combined in contact one with another in parallel to a direction of magnetization in such a manner that south and north poles of the adjacent magnets are reversed alternately (FIG. 1C: 15 mm in longitudinal length×14 mm in transversal length×4 mm in width) were prepared. Further, "magnetic material D" composed of five magnets each having a size of 3 mm in longitudinal length×14 mm in transversal length×4 mm in width combined in contact one with another in parallel to a direction of magnetization in such a manner that south and north poles of the adjacent magnets are reversed alternately (FIG. 1D: 15 mm in longitudinal length×14 mm in transversal length×4 mm in width) is prepared. The magnets were bound to each other by the holding power between the magnets or with an adhesive.

Figure 2:
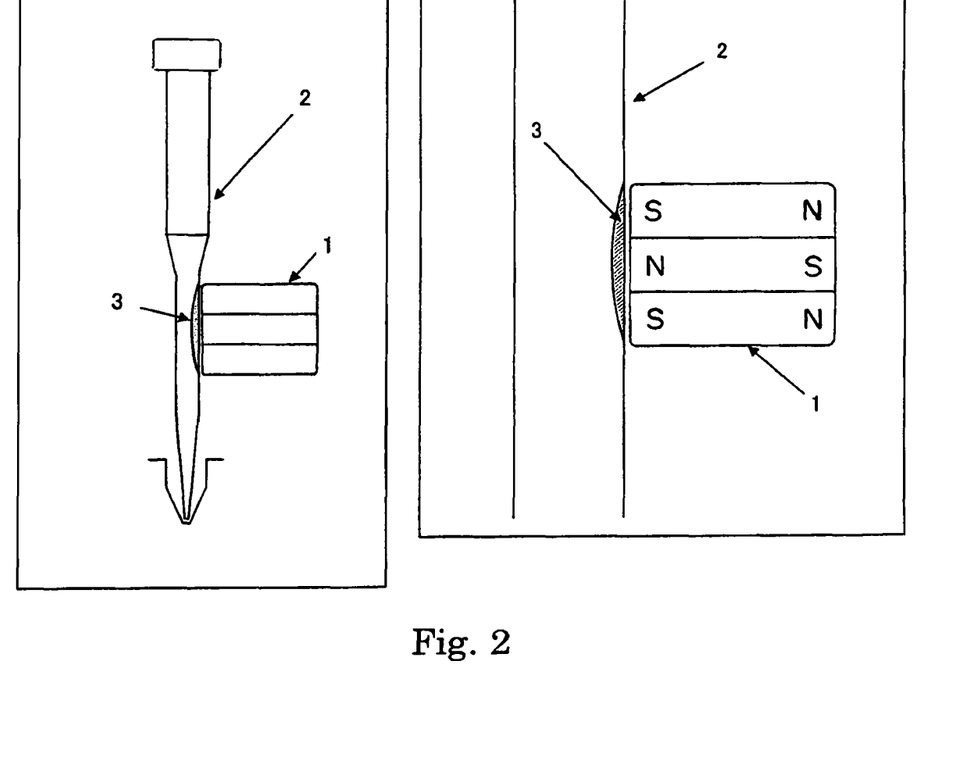
FIG. 2 is a diagram showing a state in which the magnetic material and tip of the present invention are set in an apparatus that uses the magnetic material in the step of B/F separation.

Example 2. Magnetic Particle Recovery Rate Tests Using Magnetic Material of the Present Invention Using the magnetic materials prepared in Example 1, magnetic particle recovery tests were carried out as follows.
(1) Equipment and Reagents and so on Used In the tests, a nucleic acid extracting apparatus SX-6G manufactured by Precision System Science Corporation was used. This apparatus was designed to perform extraction of nucleic acids using magnetic particles and incorporated therein a magnetic material used in the step of B/F separation. This magnetic material was replaced with each of the magnetic materials prepared in Example 1 and the magnetic particle recovery tests were performed. FIG. 2 shows the state in which the magnetic material (1) and the tip (2) were set in the apparatus.

The tip for performing sucking/discharging, set in the apparatus were disposable tip (2) made of polypropylene and had an inner diameter of about 2.25 mm and a wall thickness of about 0.75 mm at the site where the magnetic particles (3) are collected (magnetic force site). An automatic measuring cartridge having eight vessels connected thereto was used as the automatic measuring cartridge.

The solutions containing magnetic particles used were three types of commercially available solutions containing magnetic particles, i.e., a solution containing magnetic particles having carried thereon HTLV-1 antigen (hereinafter, also referred to as "HTLV-1 magnetic particle reagent": Lumipulse HTLV-1, manufactured by FUJIREBIO), a solution containing magnetic particles having carried thereon TP-N antigen (hereinafter, also referred to as "TP-N magnetic particle reagent": Lumipulse II TP-N, manufactured by FUJIREBIO), and a solution containing magnetic particles having carried thereon no antigen (RP-M1: manufactured by Rohne Poulenc). A commercially available B/F washing solution (Lumipulse washing solution, LOT NO. JJ2080, manufactured by FUJIREBIO) was used as the washing solution for B/F separation.

The recovery of magnetic particles was evaluagted by absorbance. The measurement of the absorbance of the solutions was performed using a spectrophotometer Multiskan MS (manufactured by Labsystem Corporation).

Figure 3:
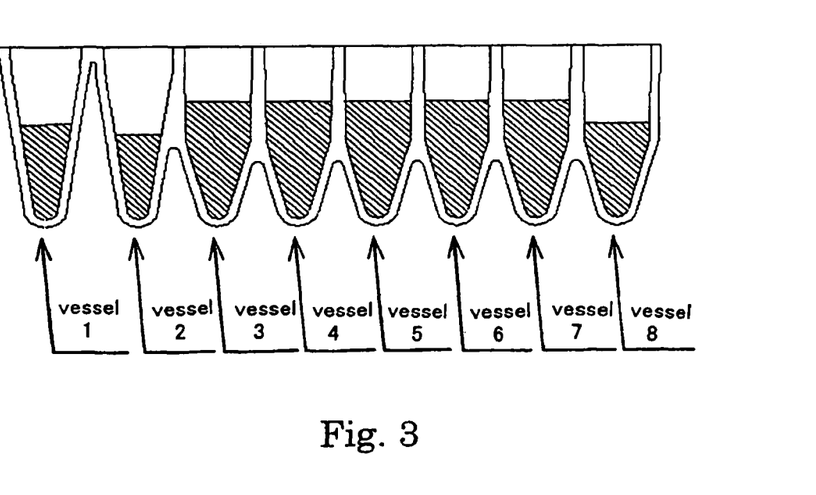
FIG. 3 is a cross-section of a cartridge for an automatic measurement including eight vessels.

(2) Measuring Method i) The solutions were filled in the automatic measuring cartridge (FIG. 3) as follows:

Vessel 1: B/F washing solution (100 μl)
Vessel 2: Solution containing magnetic particles (150 μl)
Vessel 3: B/F washing solution (500 μl)
Vessel 4: B/F washing solution (500 μl)
Vessel 5: B/F washing solution (500 μl)
Vessel 6: B/F washing solution (500 μl)
Vessel 7: B/F washing solution (500 μl)
Vessel 8: B/F washing solution (200 μl)

ii) The cartridge filled with the solution in i) above was set in SX-6G and experiments were performed according to the steps 1 to 27 below.

(step 1) Suck 100 μl of the sample solution from the vessel 1 and discharge the sample solution in the vessel 2.
(step 2) Stir and mix the solution by suction and discharging of the solution in the vessel 2.
(step 3) Perform B/F separation in the vessel 2.
(step 4) Move the tip to the vessel 3 with the magnetic particles being collected in the tip.
(step 5) Remove the magnetic material from the tip in the vessel 3.
(step 6) Stir the solution by suction and discharging to disperse the magnetic particles in the vessel 3.
(step 7) Perform B/F separation in the vessel 3.
(step 8) Move the tip to the vessel 4 with the magnetic particles being collected in the tip.
(step 9) Remove the magnetic material from the tip in the vessel 4.
(step 10) Stir the solution by suction and discharging to disperse the magnetic particles in the vessel 4.
(step 11) Perform B/F separation in the vessel 4.
(step 12) Move the tip to the vessel 5 with the magnetic particles being collected in the tip.
(step 13) Remove the magnetic material from the tip in the vessel 5.
(step 14) Stir the solution by suction and discharging to disperse the magnetic particles in the vessel 5.
(step 15) Perform B/F separation in the vessel 5.
(step 16) Move the tip to the vessel 6 with the magnetic particles being collected in the tip.
(step 17) Remove the magnetic material from the tip in the vessel 6.
(step 18) Stir the solution by suction and discharging to disperse the magnetic particles in the vessel 6.
(step 19) Perform B/F separation in the vessel 6.
(step 20) Move the tip to the vessel 7 with the magnetic particles being collected in the tip.
(step 21) Remove the magnetic material from the tip in the vessel 7.
(step 22) Stir the solution by suction and discharging to disperse the magnetic particles in the vessel 7.
(step 23) Perform B/F separation in the vessel 7.
(step 24) Move the tip to the vessel 8 with the magnetic particles being collected in the tip.
(step 25) Remove the magnetic material from the tip in the vessel 8.
(step 26) Stir the solution by suction and discharging to disperse the magnet particles in the vessel 8.
(step 27) measure the solution dispersed in the vessel 8 using a spectrophotometer.

In the above-mentioned steps, to "remove the magnetic material from the tip" means to release the magnetic material that has contacted to the tip to remove the influence of the magnetic force exerted thereon, thereby discharging the magnetic particles adsorbed and held on the inner surface of the tip into the vessel.

In the above-mentioned steps, "B/F separation" includes five steps:

a) setting a magnetic material to a tip (contacting the magnetic material with the tip),
b) B/F sucking 1: sucking a solution to pass the magnetic force site: flow rate A [μl/sec],
c) B/F discharging 1: discharging a solution to pass the magnetic force site: flow rate B [μl/sec],
d) B/F sucking 2: sucking a solution to pass the magnetic force site: flow rate C [μl/sec], and
e) B/F discharging 2: discharging a solution to pass the magnetic force site: flow rate D [μl/sec].

That is, the solution was sucked and discharged twice in a state where the magnetic material contacted the tip (in a state where the magnetic particles were adsorbed and held on the inner wall surface of the tip). The flow rate and duration of sucking/discharging were set based on the total time for performing B/F separation (time in which the magnetic particles were adsorbed and held (collection time), as follows:

<In the Case of Collection Time of 80 sec>
B/F sucking 1: flow rate A=32 μl/sec, duration=20 sec
B/F discharging 1: flow rate B=32 μl/sec, duration=20 sec
B/F sucking 2: flow rate C=32 μl/sec, duration=20 sec
B/F discharging 2: flow rate D=32 μl/sec, duration=20 sec <In the Case of Collection Time of 160 Sec>
B/F sucking 1: flow rate A=16 μl/sec, duration=40 sec
B/F discharging 1: flow rate B=16 μl/sec, duration=40 sec
B/F sucking 2: flow rate C=16 μl/sec, duration=40 sec
B/F discharging 2: flow rate D=16 μl/sec, duration=40 sec <In the Case of Collection Time of 240 Sec>
B/F sucking 1: flow rate A=10.7 μl/sec, duration=60 sec
B/F discharging 1: flow rate B=10.7 μl/sec, duration=60 sec
B/F sucking 2: flow rate C=10.7 μl/sec, duration=60 sec
B/F discharging 2: flow rate D=10.7 μl/sec, duration=60 sec iii) For the HTLV-1 magnetic particle reagent, experiments were performed using the magnetic materials A and B and setting three types of time in which the magnetic particles were adsorbed and held (collection time) to 80 sec, 160 sec, and 240 sec. For the TP-N magnetic particle reagent, measurements were performed using the magnetic materials A, B, and C and setting three collection times of 80 sec, 160 sec, and 240 sec, respectively. For the magnetic particles having carried thereon no antigen (RP-M1: manufactured by Rohne Poulenc) were measured using the magnetic materials A, B, and D and setting three collection times of 80 sec, 160 sec, and 240 sec, respectively.

The measurement of absorbance was performed at a measuring wavelength of 490 nm.

(3) Analyses and Results

Using the measured values obtained in (2) above, the recovery rate of the magnetic particles was obtained according to the following equation.

$$\text{Magnetic particle recovery rate (\%)} = ((B-b)/(A-a)) \times (200/150) \times 100$$

In the above equation, "A" is an absorbance of the solution containing the magnetic particles obtained in advance before the measurement, "a" is an absorbance of the dispersant obtained in advance before the measurement, "B" is an absorbance of the solution containing the magnetic particles obtained as a result of the measurement, and "b" is an absorbance of the B/F washing solution that serves as the dispersant for the magnetic particles in the vessel 8. As the value a, the absorbance obtained by separately isolating two types of the solutions containing the magnetic particles described in (2) above, centrifuging the solutions to recover only the dispersant as a supernatant, and measuring the supernatant was used. The "(200/150)" is a correction of volume. That is, the amount of the solution in which the magnetic particles were first contained is 150 µl (vessel 2), from which the magnetic particles were recovered by the magnetic force, and finally dispersed in 200 µl of the solution (vessel 8), and the absorbance was measured. From this, the obtained absorbance was multiplied with a liquid amount ratio of 200/150 to correct the amount of the liquid, thus obtaining the recovery rate.

Figure 4:
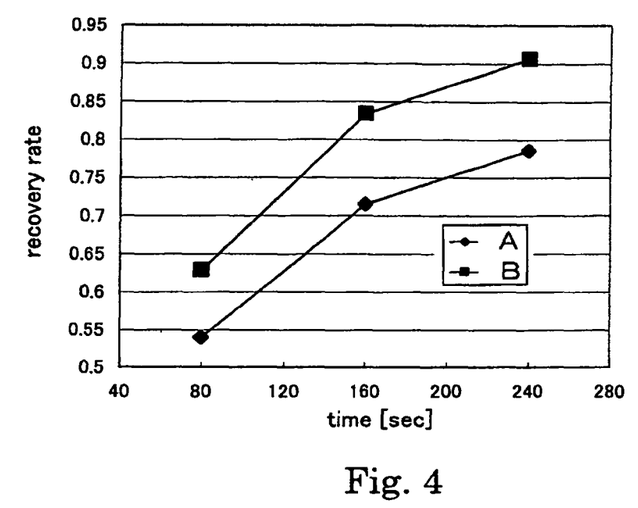
FIG. 4 is a graph illustrating the recovery rates of HTLV-1 magnetic particles with magnetic materials A and B, with the vertical axis representing recovery rate (unit: %×1/100), and the horizontal axis representing time (unit: second), where the results obtained by using the magnetic material A are indicated by diamonds, and the results obtained by using the magnetic material B are indicated by squares.
Figure 5:
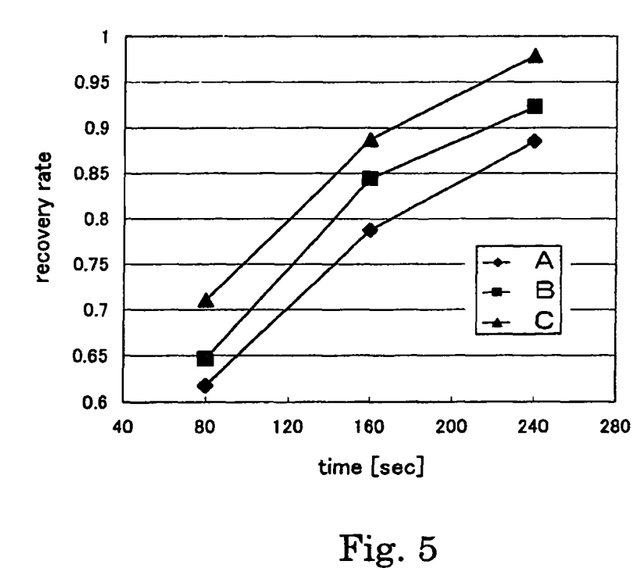
FIG. 5 is a graph illustrating the recovery rates of TP-N magnetic particles with magnetic materials A, B, and C, respectively, with the vertical axis representing recovery rate (unit: %×1/100), and the horizontal axis representing time (unit: second), where the results obtained by using the magnetic material A are indicated by diamonds, the results obtained by using the magnetic material B are indicated by squares, and the results obtained by using the magnetic material C are indicated by triangles.
Figure 6:
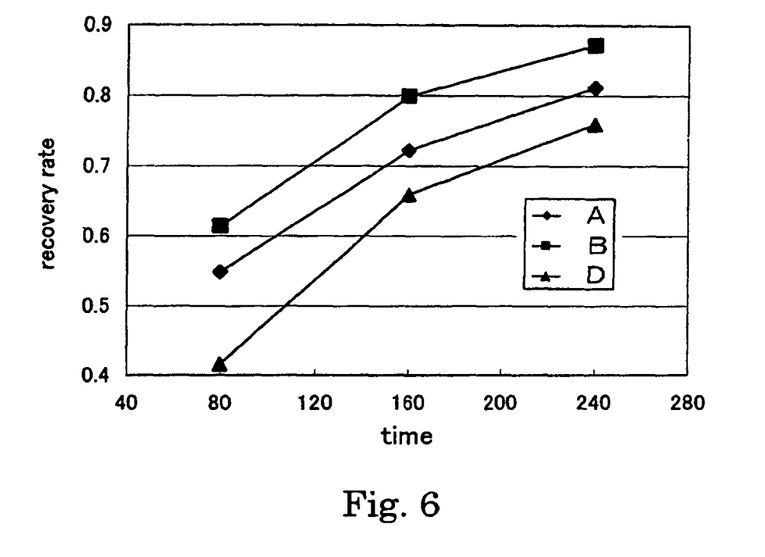
FIG. 6 is a graph illustrating the recovery rates of the magnetic particles having carried no antigen with magnetic materials A, B, and D, with the vertical axis representing recovery rate (unit: %×1/100), and the horizontal axis representing time (unit: second), where the results obtained by using the magnetic material A are indicated by diamonds, the results obtained by using the magnetic material B are indicated by squares, and the results obtained by using the magnetic material D are indicated by triangles.

The results of the measurements using the HTLV-1 magnetic particle reagent are shown in Table 1 and the results in the form of a graph are illustrated in FIG. 4. The results of the measurements using the TP-N magnetic particle reagent are shown in Table 2 and the results in the form of a graph are illustrated in FIG. 5. The results of the measurement using the magnetic particles having carried thereon no antigen (RP-M1: manufactured by Rohne Poulenc) are shown in Table 3 and the results in the form of a graph are illustrated in FIG. 6.

TABLE 1

| Magnetic material | Collection time [sec] | | |
|---|---|---|---|
| | 80 | 160 | 240 |
| A | 54.0% | 71.5% | 78.6% |
| B | 62.9% | 83.4% | 90.7% |

TABLE 2

| Magnetic material | Collection time [sec] | | |
|---|---|---|---|
| | 80 | 160 | 240 |
| A | 61.8% | 78.7% | 88.5% |
| B | 64.6% | 84.4% | 92.3% |
| C | 71.0% | 88.7% | 97.9% |

TABLE 3

| Magnetic material | Collection time [sec] | | |
|---|---|---|---|
| | 80 | 160 | 240 |
| A | 54.9% | 72.2% | 81.2% |
| B | 61.4% | 79.9% | 87.2% |
| D | 41.6% | 65.9% | 76.0% |

The results of the experiments using the HTLV-1 magnetic particle reagent and the TP-N magnetic particle reagent indicate that by using either types of the magnetic particles, the layered magnetic materials B and C could collect the magnetic particles much more efficiently than the magnetic material A consisting of a single magnet. When the collection time was prolonged, higher recovery rates were obtained and a high recovery rate of 90% or more was achieved at 240 sec.

On the other hand, the experiments using magnetic particles having carried thereon no antigen indicate that the magnetic material D consisting of five magnets layered exhibited a decreased collection efficiency of magnetic particles, which was lower than those of the magnetic materials A and B.

Example 3. Immunoassay Using Magnetic Material of the Present Invention

Using the magnet materials prepared in Example 1 above, an immunoassay using magnetic particles was performed and the results obtained were analyzed.

(1) Equipment and Reagents and so on Used

The apparatus, the magnetic material, the tip and the cartridge were the same as those used in Example 2 above were employed. The magnetic materials A and C prepared in Example 1 were used as the magnetic material.

Samples containing HBs antigen (Lot No. NW3011, manufactured by FUJIREBIO, in two different concentrations) were measured using magnetic particles having carried thereon an HBs antibody (hereinafter, also referred to as "HBs-Ag magnetic particle reagent"): Lumipulse H HBs-Ag, Lot No. NC3022, manufactured by FUJIREBIO) as the magnetic particles. Also, samples containing an HIV antibody (Lot No. CD0085, manufactured by FUJIREBIO) were measured using the magnetic particles having carried thereon an HIV antigen (hereinafter, also referred to as "HIV magnetic particle reagent", Lumipulse ortho HIV-1/2, Lot No. CD2104, manufactured by FUJIREBIO).

(2) Measuring Method i) The solutions were filled in the automatic measuring cartridge (FIG. 3) as follows:
  Vessel 1: Sample solution (100 pd)
  Vessel 2: Solution containing magnetic particles (150 µl)
  Vessel 3: B/F washing solution (500 µl)
  Vessel 4: B/F washing solution (500 µl)
  Vessel 5: Labeled secondary antibody solution (ALP) (250 µl)
  Vessel 6: B/F washing solution (500 µl)
  Vessel 7: B/F washing solution (500 µl)
  Vessel 8: Luminescent substrate solution (200 µl)

ii) The cartridge filled with the solution in i) above was set in SX-6G and measurements were performed according to the steps 1 to 27 below. The measurement was performed three times for each sample.

(step 1) Suck 100 µl of the sample solution from the vessel 1 and discharge the sample solution in the vessel 2.

(step 2) In the vessel 2, stir the solution by suction and discharging and mix the sample solution and the solution containing the magnetic particles to perform a first antigen-antibody reaction.

(step 3) Perform B/F separation in the vessel 2.

(step 4) Move the tip to the vessel 3 with the magnetic particles being collected in the tip.

(step 5) Remove the magnetic material from the tip in the vessel 3.

(step 6) Stir the solution by suction/discharging of the solution in the vessel 3 to disperse the magnetic particles.

(step 7) Perform B/F separation in the vessel 3.

(step 8) Move the tip to the vessel 4 with the magnetic particles being collected in the tip.

(step 9) Remove the magnetic material from the tip in the vessel 4.

(step 10) Stir the solution by suction and discharging to disperse the magnetic particles in the vessel 4.

(step 11) Perform B/F separation in the vessel 4.

(step 12) Move the tip to the vessel 5 with the magnetic particles being collected in the tip.

(step 13) Remove the magnetic material from the tip in the vessel 5.

(step 14) In the vessel 5, suck and discharge the labeled secondary antibody solution to disperse the magnetic materials in a state where the magnetic particles were adsorbed and held on the inner wall surface of the tip so that the magnetic particles specifically bind to the test substance to perform a second antigen-antibody reaction to generate an immune complex.

(step 15) Perform B/F separation in the vessel 5.

(step 16) Move the tip to the vessel 6 with the magnetic particles being collected in the tip.

(step 17) Remove the magnetic material from the tip in the vessel 6.

(step 18) Stir the solution by suction and discharging to disperse the magnetic particles in the vessel 6.

(step 19) Perform B/F separation in the vessel 6.

(step 20) Move the tip to the vessel 7 with the magnetic particles being collected in the tip.

(step 21) Remove the magnetic material from the tip in the vessel 7.

(step 22) Stir the solution by suction and discharging to disperse the magnetic particles in the vessel 7.

(step 23) Perform B/F separation in the vessel 7.

(step 24) Move the tip to the vessel 8 with the magnetic particles being collected in the tip.

(step 25) Remove the magnetic material from the tip in the vessel 8.

(step 26) Stir the solution by suction and discharging of the luminescent substrate solution to disperse the magnetic material in the vessel 8.

(step 27) React CDP-STAR (manufactured by Tropix) on ALP contained in the immune complex generated in (step 14) and measure the generated signal using a photomultiplier.

(3) Analysis and Results

From the measured values (luminescence counts (cps)) of three runs obtained in (2) above, average values (Avg), standard deviation (SD), and coefficient of variation (cv) were obtained.

The results of the measurements with the HBs-Ag magnetic particle reagent are shown in Table 4 and the results of the measurements with the HIV magnetic particle reagent are shown in Table 5.

TABLE 4

|  | Magnetic material A | | Magnetic material C | |
|---|---|---|---|---|
|  | sample1 | sample2 | sample1 | sample2 |
| 1 | 450,432 | 914,780 | 460,100 | 904,000 |
| 2 | 464,784 | 930,256 | 449,148 | 918,428 |
| 3 | 476,916 | 907,780 | 456,604 | 917,352 |
| Avg | 464,044 | 917,605 | 455,284 | 913,260 |
| SD | 13,257.5 | 11,501.3 | 5,594.0 | 8,037.4 |
| cv(%) | 2.9% | 1.3% | 1.2% | 0.9% |

TABLE 5

|  | Magnetic material A Sample1 | Magnetic material C sample1 |
|---|---|---|
| 1 | 437,252 | 451,740 |
| 2 | 467,888 | 463,520 |
| 3 | 505,796 | 468,128 |
| Avg | 470,312 | 461,129 |
| SD | 34,336.2 | 8,451.5 |
| cv(%) | 7.3% | 1.8% |

The results of the analyses indicate that in the immunoassays using either one of the magnetic particles, use of the magnetic material C of the present invention enabled measurements much more stable than the measurements with the single magnet-magnetic material A and showed a high reproducibility.

Example 4. Analysis of Magnetic Force Distribution on Pole Surface of Magnetic Material of the Present Invention In Examples 1 to 3, the effects of the magnetic material of the present invention having a plurality of magnets layered were confirmed. Accordingly, further detailed analysis of the magnetic force was performed on the magnetic materials A, B, C, and D prepared in Example 1 above.

Figure 7:
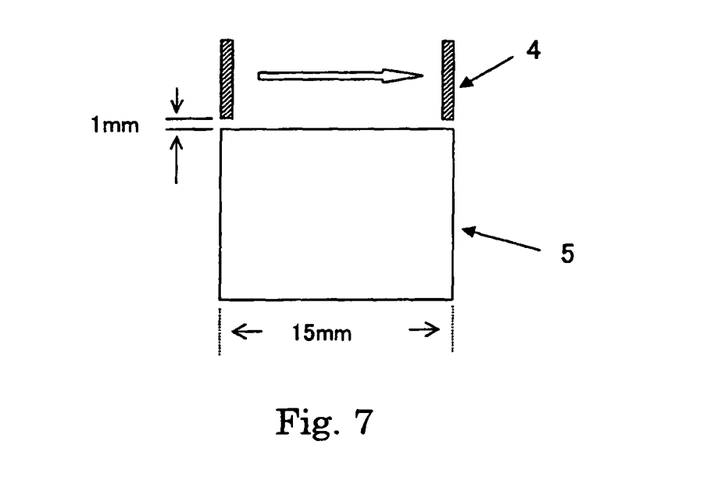
FIG. 7 is a diagram illustrating the position of a measuring probe with respect to the magnetic material in the measurement of the magnetic force of the magnetic material with a handy Gauss meter.

The magnetic force of each magnetic material was measured using a handy gauss meter (MODEL 4048: manufactured by F. W. BELL) and a measuring probe (T-4048-001 Type: manufactured by F. W. BELL). First, as shown in FIG. 7, a measuring portion of a probe (4) was set vertically on a pole surface of a magnetic material (5), which is a target to be measured, at a distance of 1 mm from the magnetic pole surface. The magnetic materials A, B, and C were measured for the magnetic force at respective points while moving the measuring probe by 2.5 mm from one end to the other end of the magnetic pole surface. The magnetic material D was measured for the magnetic force at respective points while moving the magnetic material by 1.5 mm from one end to the other end of the magnetic pole surface.

Figure 8:
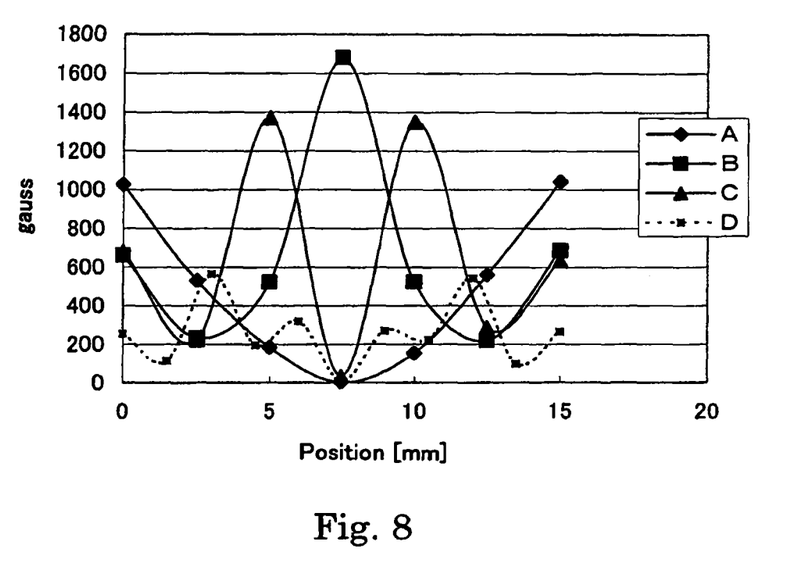
FIG. 8 is a graph illustrating measurement results of magnetic force on the position of the magnetic pole surface, with the vertical axis representing magnetic force (unit: gauss), and the horizontal axis representing the position of the magnetic pole surface (unit: mm), where the results obtained by using the magnetic material A are indicated by diamonds, the results obtained by using the magnetic material B are indicated by squares, the results obtained by using the magnetic material C are indicated by triangles, and these results are indicated by solid lines, respectively, and the results obtained by using the magnetic material D are indicated by smaller squares and broken line.

The results of the measurements are shown in Table 6 and FIG. 8.

TABLE 6

| position in a magenetic pole surface [mm] | Magnetic force (Static magnetic field: gauss) | | | |
|---|---|---|---|---|
|  | A | B | C | D |
| 0 | 1027 | 661 | 683 | 255 |
| 1.5 |  |  |  | 113 |
| 2.5 | 532 | 233 | 223 |  |

TABLE 6-continued

| | Magnetic force (Static magnetic field: gauss) | | | |
|---|---|---|---|---|
| position in a magenetic pole surface [mm] | A | B | C | D |
| 3 | | | | 566 |
| 4.5 | | | | 196 |
| 5 | 184 | 522 | 1371 | |
| 6 | | | | 320 |
| 7.5 | 2.8 | 1679 | 34.4 | 6.3 |
| 9 | | | | 272 |
| 10 | 154 | 523 | 1350 | |
| 10.5 | | | | 225 |
| 12 | | | | 542 |
| 12.5 | 561 | 219 | 290 | |
| 13.5 | | | | 98 |
| 15 | 1042 | 686 | 635 | 266 |

As the results of measurement, graphical representation of the measurements for the magnetic force continuously measured at pole surfaces of the respective magnetic materials indicates as shown in FIG. 8 that the magnetic materials had their own peaks of magnetic force and number of peaks. In the magnetic material A, which is a single magnet-magnetic material, a strong magnetic force was observed only at the end of the magnetic material. On the other hand, the magnetic material B having layered two magnets had a peak of magnetic force in one layered portion of the magnets that is present in the pole surface of the magnetic material besides the peaks at the both ends of the magnetic material and a strong magnetic force of 1,000 gausses or more was measured. The magnetic material C having layered three magnets had peaks of magnetic force in two layered portions that are present in the pole surface of the magnetic material besides the peaks at the both ends of the magnetic material and a strong magnetic force of 1,000 gausses or more was measured. However, in the case of the magnetic material D having layered five magnets had peaks of magnetic force at four layered portions that are present in the center of the magnetic material besides the two peaks at the both ends of the magnetic material and the every peak has a low magnetic force of 600 gausses or less, thus showing no clear peak shapes.

These results demonstrate that the magnetic materials of the present invention have properties of exhibiting strong magnetic force not only on the end(s) of the magnetic material but also at layered portions of the magnets. From the lack of strong magnetic force peaks of above 600 gausses in the magnetic material D and the small, unclear shapes of the peaks, it was conceived that when a magnetic material having an outer size on the order of 15 mm in longitudinal length×14 mm in transversal length×4 mm in width, use of five or more magnets leads to an insufficient magnetic force. The size of the magnetic material of the present invention can be determined to have an optimum configuration taking into consideration the results of such measurements as indicator. These results coincide with the results obtained in Examples 2 and 3. That is, the magnetic materials B and C of the present invention have at least one magnetic force peak in the magnetic pole surface besides peaks at the ends of the magnetic material, and the magnetic force thereof is as high as 1,000 gausses or more. This indicates that the magnetic materials B and C had an ability to collect the magnetic particles more efficiently than the magnetic material A, which is a single magnet-magnetic material.

On the other hand, the magnetic material D has a peak of magnetic force in the magnetic pole surface, but the peak magnetic force is 600 gausses or less and is insufficient. When the magnetic material D was used, the recovery rate of the magnetic particles decreased as compared with that of the magnetic material A.

The results obtained in Examples 1 to 4 confirms two major features of the magnetic materials of the present invention, (1) strong magnetic forces can be generated not only on the ends of the magnetic material but also in the layered portions of the magnets, and (2) the magnetic lines accumulate near the magnetic pole surface and the magnetic force can be effectively exerted onto a tip or the like used as a liquid suction line. Accordingly, the magnetic materials are particularly useful for collecting the magnetic particles.

INDUSTRIAL APPLICABILITY

By using the magnetic material of the present invention and the method of collecting the magnetic particles according to the present invention, collection of the magnetic particles can be performed with a very high accuracy, stably and at a high speed. This makes it possible to perform measurements with a high accuracy even in an immunoassays etc. that require B/F separation in a plurality of times. Also, the present invention allows down-sizing of the magnetic material, so that the apparatus can reduce its size.

The invention claimed is:

1. A method of collecting magnetic particles, the method comprising:
    adsorbing and holding magnetic particles in a liquid on a wall surface by a magnetic force and then
    making the magnetic particles unaffected by the magnetic force to release the magnetic particles,
    wherein the adsorbing and holding comprises generating the magnetic force from a magnetic material suitable for collecting the magnetic particles,
    wherein the magnetic material comprises a plurality of magnets that are arranged in contact with one another in parallel to a direction of magnetization in such a manner that south and north poles of adjacent magnets are reversed alternately, and
    wherein the number of magnets in the plurality of magnets is two or three.

2. The method according to claim 1, wherein the wall surface is an inner wall surface of a liquid suction line of a dispenser that sucks a liquid from a vessel and discharges the liquid.

3. The method according to claim 1, wherein the magnetic particles are suitable for performing an immunoassay.

4. The method according to claim 2, wherein the absorbing and holding further comprises facing a surface of the magnetic material in which the south and north poles of the adjacent magnets are reversed alternately to the inner wall surface of the liquid suction line of the dispenser.

5. The method according to claim 1, wherein the magnetic material has at least one peak of a magnetic force at a boundary of the magnets in a magnetic pole surface.

6. The method according to claim 5, wherein a magnetic force at the at least one peak is 1,000 gausses or more.

* * * * *